(12) United States Patent
Shah et al.

(10) Patent No.: US 6,473,659 B1
(45) Date of Patent: Oct. 29, 2002

(54) SYSTEM AND METHOD FOR INTEGRATING A PLURALITY OF DIAGNOSTIC RELATED INFORMATION

(75) Inventors: Rasiklal Punjalal Shah, Latham, NY (US); Vipin Kewal Ramani, Niskayuna, NY (US); Susan Teeter Wallenslager, Waukesha, WI (US); Christopher James Dailey, Summerville, SC (US)

(73) Assignee: General Electric Company, Schenectady, NJ (US)

( * ) Notice: Subject to any disclaimer, the term of this patent is extended or adjusted under 35 U.S.C. 154(b) by 0 days.

(21) Appl. No.: 09/058,755

(22) Filed: Apr. 10, 1998

(51) Int. Cl.$^7$ .................................................. G05B 9/02
(52) U.S. Cl. ........................... 700/79; 702/179; 714/25; 714/26; 382/141; 382/157
(58) Field of Search ............................... 700/79; 714/25, 714/26, 37; 706/62, 10, 22; 382/141, 157; 702/34, 35, 179, 183

(56) References Cited

U.S. PATENT DOCUMENTS

| | | | | |
|---|---|---|---|---|
| 4,853,946 A | * | 8/1989 | Hartness et al. ............... 53/539 |
| 4,967,337 A | * | 10/1990 | English et al. ............... 364/184 |
| 5,077,768 A | * | 12/1991 | Shigyo et al. ................. 378/98 |
| 5,303,361 A | * | 4/1994 | Colwell et al. ................. 707/4 |
| 5,602,761 A | * | 2/1997 | Spoerre et al. ............. 702/179 |
| 5,651,362 A | * | 7/1997 | Schulz, Jr. et al. ......... 524/862 |
| 5,754,451 A | * | 5/1998 | Williams ..................... 702/185 |
| 5,761,278 A | * | 6/1998 | Pickett et al. ............ 379/90.01 |
| 5,819,296 A | * | 10/1998 | Anderson et al. ........... 707/204 |
| 5,924,090 A | * | 7/1999 | Krellenstein .................... 707/5 |
| 5,949,676 A | * | 9/1999 | Elsley .......................... 700/79 |
| 6,105,149 A | * | 8/2000 | Bonissone et al. ............ 714/26 |
| 6,115,489 A | * | 9/2000 | Gupta et al. ................ 382/141 |

* cited by examiner

*Primary Examiner*—James P. Trammell
*Assistant Examiner*—Firmin Backer
(74) *Attorney, Agent, or Firm*—David C. Goldman; Jill M. Breedlove

(57) ABSTRACT

This invention provides a system and method for integrating a plurality of diagnostic information from a multiple of sources. In this invention, there is a site specific database which contains site specific information for a machine. A plurality of diagnostic related information is obtained from the machine. A diagnostic router collects the site specific information for the machine and the plurality of diagnostic related information and generates a current incident record therefrom. An approved incident record database contains a plurality of approved incident records obtained from a plurality of machines. An integrator finds approved incident records from the approved incident record database that most closely match the current incident record.

60 Claims, 7 Drawing Sheets

```
[@SITE]
SystemID=NSCUL700
Site=MILWAUKEE OFFICE
Model=LOGIQ700
Modality=UL
[@END]
[@IR]
crName=modi
feName=
clName=
crDate=1/27/1998 2:45
enDate=1/27/1998 2:45
clDate=
Probe=618e
valid=No
Resolution=No
[@END]
[@IMAGE]
No. of Files=1
[@TOOL]
ToolName=IDIA
File Name=SCREEN-97.04.07_10:37:09-IUO
[@END]
[@END]
[@Error]
No. of Files=2
[@TOOLS]
ToolName=ELSI
FileName=Error.LOG-94.10.26_12:37:18-EUO
[@END]
[@TOOL]
ToolName=ELSI
FileName=Error.LOG-94.11.29_10:44:33-EUO
[@END]
[@END]
[@POWER]
No. of Files=0

[@END]
[@TEMP]
No.of Files=0
[@END]
[@ACTIONS]
[@END]
```

Site Informations
- System ID: 808621L700
- Site Name: General Hospital
- Integrator:
- FE Name:
- SE Name:
- Model Type: LOGIQ 700
- Probe Type: 618e

Tool Recommendations

| Tool | FileName | FRU/Service Action/Artifact | Confidence |
|---|---|---|---|
| ELSI | Error.LOG-96.01.04_20:14:47-EUO | HOSPITAL_GROUNDING_ISSUE | 0.43 |
| IDIA | SCREEN-96.01.29_15:23:15-IUO | TD08/Cyst/ | 0.17 |
| IDIA | SCREEN-96.01.29_15:23:15-IUO | Bench/Cyst/ | 0.17 |
| IDIA | SCREEN-96.01.29_15:23:15-IUO | Bench/Center/ | 0.17 |

View Log

Integrator

Weight
- [✓] Default
- [ ] User Difined
- [ ] Equal Weights

Tool & Weight
- ELSI  1.0
- IDIA  1.0

Integrate

Assign Tool Weight: 1.0

Integrated Recommendations

| Incident Record | Date | Fix | Confidence |
|---|---|---|---|
| 808621L700_87254686153 6.IR | 08:25:97 1347 | Site Power Supply | 63.64 |
| 808621L700_87260188963 1.IR | 12:08:96 1456 | Site Power Supply | 34.76 |
| 808621L700_87236665767 5.IR | 06:26:97 1430 | Replace Probe | 21.06 |
| 808621L700_87235452559 8.IR | 08:28:97 0900 | Replace TD08 | 17.60 |
| 808621L700_87251492810 7.IR | 08:24:97 1230 | Replace TD08 | 17.60 |

View Matching IR's

Actual Fix
Site Power Supply ▼

Table Of Contents ▼

Done

80

SYSTEM AND METHOD FOR INTEGRATING A PLURALITY OF DIAGNOSTIC RELATED INFORMATION

FIELD OF THE INVENTION

The present invention relates generally to fault diagnosis and more particularly to integrating a plurality of diagnostic related information in order to facilitate detection and identification of a fault and recommend a service or control action for a machine experiencing a failure, a fault condition, or symptoms of an incipient failure condition or mode.

BACKGROUND OF THE INVENTION

In either an industrial or commercial setting, a malfunctioning machine can impair a business severely. Thus, it is essential that a malfunctioning machine be repaired quickly and accurately. For example, during a malfunction of an imaging machine such as an ultrasound, a computed tomography (CT), or a magnetic resonance imaging (MRI) machine, a field engineer is called in to diagnose and repair the machine. Typically, the field engineer will look at multiple sets of information generated from the imaging machine. For example, there is an error log generated from the imaging machine which contains sequences of events that occurred during both routine operation as well as during any malfunction situation. The error log represents a "signature" of the operation of the machine and can be used to correlate malfunctions. In addition, there are a series of phantom images and clinical images generated from the imaging machine. Other information includes the imaging machine's operative parameters (e.g., power, temperature, etc.) and waveform data generated from running a system performance test.

Using their accumulated experiences at solving imaging machine malfunctions, the field engineer looks through the multiple of information and tries to find any symptoms that may point to the fault. The field engineer then tries to correct the problem that may be causing the machine malfunction. If there is only a small amount of information to evaluate, then this process will work fairly well. However, if there is a large amount of information to process as is usually the case for large complex devices, it will be very difficult for the field engineer to diagnose a fault with accuracy and completeness. In this case, the field engineer will request the help of a service engineer located at a remote site for assistance in evaluating the information and thus diagnosing the most likely cause of the malfunction. Typically, the service engineer retrieves all of the information obtained from the imaging machine. At the remote site, automated tools specific to each of the imaging machine information type are available to the service engineer. The service engineer then runs a series of automated analysis and diagnosis tools to evaluate the information obtained from the imaging machine. Each of the automated analysis and diagnosis tools generates a list of recommendation(s) for diagnosing the condition for the malfunction. The service engineer analyzes the list of recommendations from the multiple tools and uses their accumulated experience at solving imaging machine malfunctions to find the most likely cause for the fault. The service engineer then recommends a particular fix action to the field engineer.

A problem with this approach is that there is no predefined execution strategy for selecting the specific analysis and diagnosis tools and executing them. A predefined execution strategy is needed because some of the analysis and diagnosis tools are more effective than others at solving a given system malfunction. Without a predefined execution strategy, it is difficult for the service engineer to determine the most likely cause for the fault. Another problem with this approach is that the recommendations generated from the analysis and diagnosis tools sometimes overlap or conflict with each other. A methodology is needed to resolve such conflicts so that the final recommendations of fault conditions are in fact the most likely actual fault and the corrective service or control action recommended is accurate. Therefore, there is a need for a system and method that can integrate knowledge from various sources of information in order to quickly detect and identify a fault, and recommend a service or control action for a machine experiencing a failure, a fault condition, or symptoms of an incipient failure condition or mode.

SUMMARY OF THE INVENTION

This invention is able to quickly detect and identify a fault, and recommend a service or control action for a machine experiencing a failure, a fault condition, or symptoms of an incipient failure condition or mode by using a diagnostic router and an integrator. The diagnostic router collects a plurality of diagnostic related information for the machine from a multiple of sources and generates a current incident record therefrom. The integrator finds approved incident records from an approved incident record database that most closely match the current incident record. A recommended service action or fix is generated by the integrator to bring the machine to a normal operating state or mode. The integrator resolves any conflicting information in order to a unique recommendation.

In accordance with this invention, there is provided a system and method for integrating a plurality of information from a multiple of sources. In this invention, there is a site specific database containing site specific information for a machine. A plurality of diagnostic related information is obtained from the machine. A diagnostic router collects site specific information for the machine from the site specific database and the plurality of diagnostic related information and generates a current incident record therefrom. An approved incident record database contains a plurality of approved incident records obtained from a plurality of machines. An integrator finds approved incident records from the approved incident record database that most closely match the current incident record.

DESCRIPTION OF THE DRAWINGS

FIG. 4 shows an example of a current incident record generated by the diagnostic router;

FIG. 6 shows an example of a graphical user-interface for the integrator; and

DETAILED DESCRIPTION OF THE INVENTION

Figure 1:
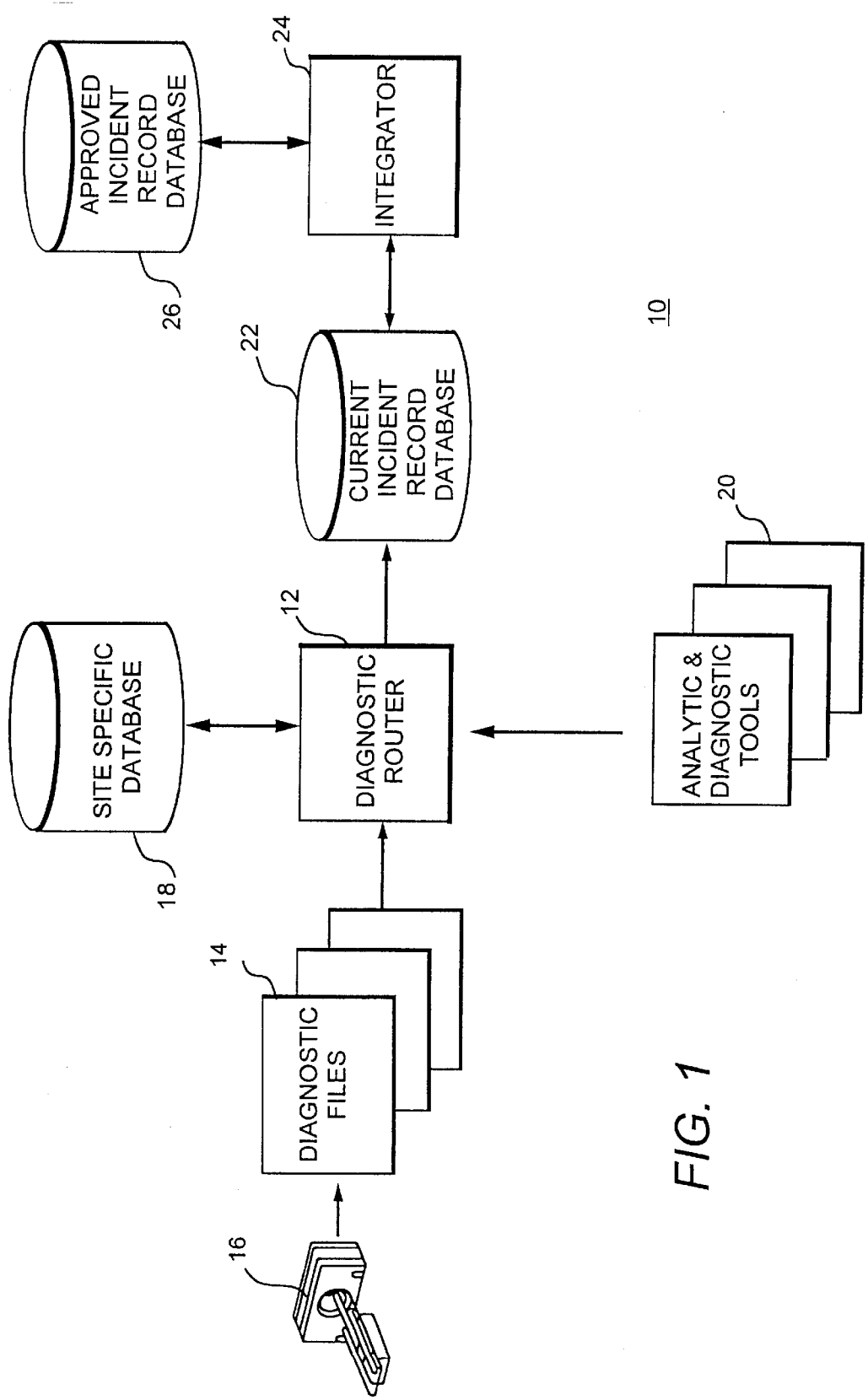
FIG. 1 shows a block diagram of a system for integrating information used for diagnosing an imaging machine according to this invention.

The information integration system of this invention is described with reference to a medical imaging device such as an ultrasound, a CT, or a MRI machine. Although this invention is described with reference to a medical imaging device, the information integration system can be used in conjunction with any device (chemical, mechanical, electronic, microprocessor controlled) or any system such as an aircraft, an aircraft engine, a turbine, a power system, a locomotive, or a computer system which generates a plurality of diagnostic information and/or uses a plurality of analytic and diagnostic tools to evaluate the information. FIG. 1 shows a block diagram of a system 10 for integrating information used for diagnosing an imaging machine according to this invention. The information integration system 10 includes a diagnostic router 12 which receives a plurality of diagnostic files 14 obtained from a machine 16 which may be located at a remote site. The diagnostic router 12 also collects site specific information for the machine 16 from a site specific database 18. A plurality of automated analytic and diagnostic tools 20 are available for the diagnostic router 12 for evaluating the diagnostic files 14. Each of the analytic and diagnostic tools generates an output which contains a list of recommendation(s) for diagnosing the condition for the malfunction. In addition, each output contains a confidence value indicating the tool's belief that the recommendation will diagnose the condition for the malfunction. The diagnostic router 12 generates a current incident record from the diagnostic files 14 and the outputs of the analytic and diagnostic tools 20.

The current incident record is stored in a current incident record database 22. An integrator 24 reads the current incident record and searches an approved incident record database 26 for approved incident records that most closely match the current incident record. Each of the approved incident records in the approved incident record database 26 contains historical tool outputs generated from the diagnostic and analytic tools 20. Before the search is initiated, the service engineer or the integrator 24 assigns a weight to each of the plurality of diagnostic and analytic tools 20. The weight is representative of the confidence in the tool to solve the current incident record. For each approved record in the incident record database 26, the integrator 24 determines a matching percentage with the current incident record according to the weights assigned to each of the diagnostic and analytic tools 20.

The integrator 24 ranks the approved incident records according to the determined matching percentage. The integrator 24 continues to rank all of the approved incident records in the approved incident record database 26 according to the matching percentage unless instructed by a service engineer to stop the search. After the search has been stopped, there are three options for the integrator 24. One option is to append the current incident record with the results from the highest ranked approved incident record and store the appended record in the current incident record database 22. The second option is to use the results from the highest ranked incident record to fix the machine 16 and add the fix information to the current incident record. This information is subsequently sent to a knowledge facilitator which decides whether the current incident record should be stored in the approved incident record database 26 and used in future cases. The third option is to cancel the results from the search.

Figure 2:
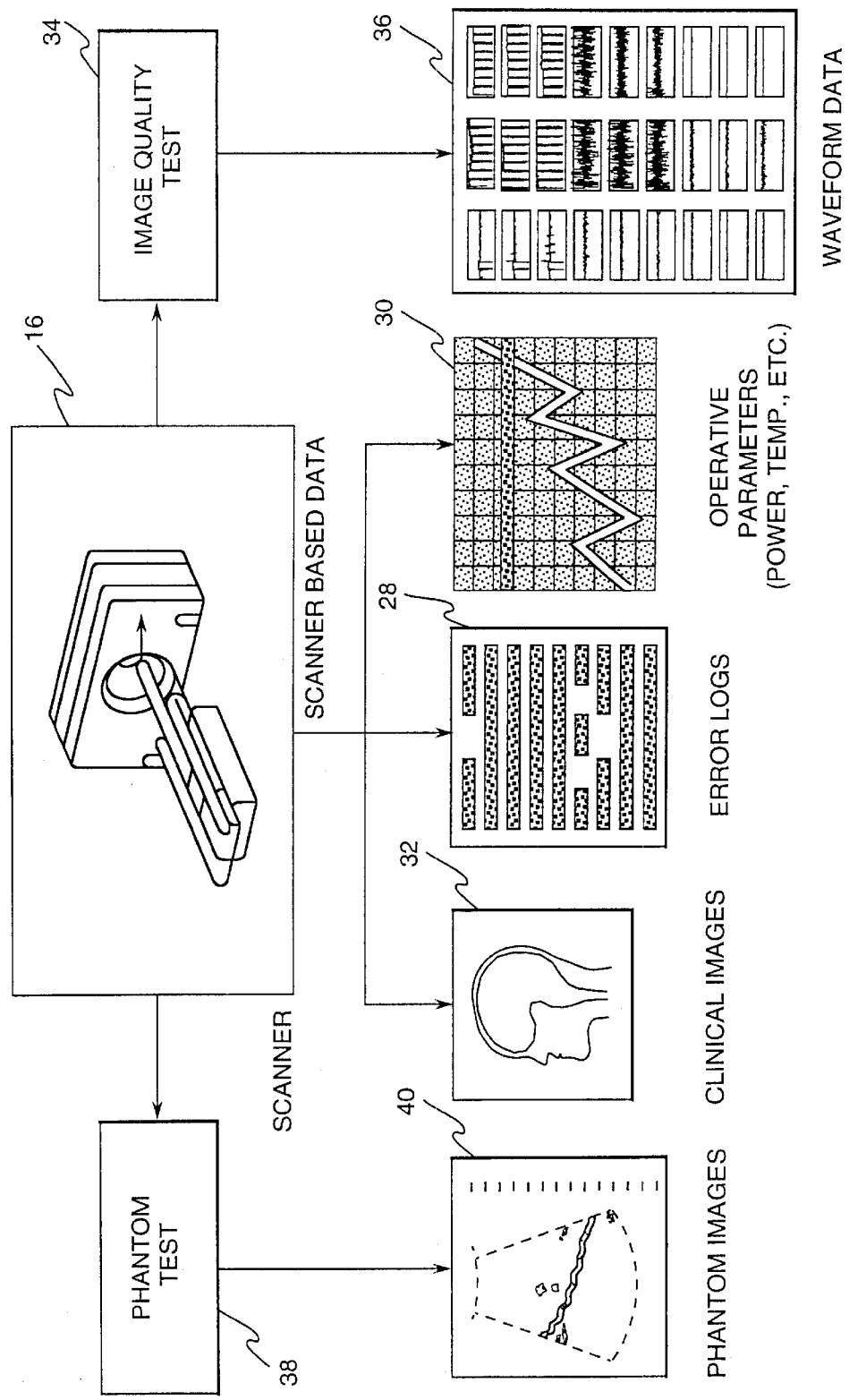
FIG. 2 shows a schematic diagram of the types of diagnostic files generated from the imaging machine shown in FIG. 1 according to this invention.

A schematic diagram of some of the plurality of diagnostic files 14 generated from the imaging machine 16 is shown in FIG. 2. Generally, the plurality of diagnostic files 14 comprise scanner-based data and test data. One type of scanner-based data is error logs 28 generated from the imaging machine. A error log contains sequences of events that occurred during both routine operation as well as during any malfunction situation. The error log represents a "signature" of the operation of the machine 16 and is used to correlate malfunctions. Another type of scanner-based data file is the imaging machine's operative parameters 30 which indicate the performance of the machine. The machine's operative parameters include power, temperature, pressure, flow, level, etc. Clinical image files 32 are another type of scanner-based data file generated by the imaging machine 16. Clinical image files comprise a variety of clinical images generated from the imaging machine 16. One type of test that is run on the imaging machine is an image quality test 34 or a system performance test. The image quality test 34 generates a series of waveform data 36 which are indicative of the image quality or the state of the machine 16. Another type of test that is run is a phantom test 38 which generates images 40 of a phantom using all possible probes and machine default parameter settings. The above diagnostic files are an illustrative list of some of the types of files and not an exhaustive list.

For each of the above diagnostic files 14, there is a corresponding analytic and diagnostic tool 20 for evaluating the information in the files. In this invention, the error logs are analyzed with an error log similarity index tool. This tool compares a new error log against blocks of historical error logs. If the new error log is found to contain block(s) similar to the blocks contained in the historical error logs, then a similarity index is determined to indicate how similar the new error log is with a historical error log. Depending on the similarity index, solution(s) used to solve the historical error log are proposed for use to solve the problem associated with the new error log. A more detailed discussion of the error log similarity index tool is set forth in commonly assigned, U.S. Pat. No. 5,463,768, entitled "Method And System For Analyzing Error Logs For Diagnostics", which is incorporated herein by reference.

The phantom images 40 and the clinical images 32 are analyzed with an image-based diagnostic tool. This tool compares the phantom images 40 and the clinical images 32 to historical images taken from a plurality of machines which are stored in a database. The historical images comprise ideal images generated from the plurality of machines using all possible machine settings. In addition, the historical images comprise artifact images generated from the plurality of machines. Each of the artifact images have known faults associated therewith and a corresponding corrective action for repairing the faults. The image-based diagnostic tool finds an ideal image from the historical images that most closely matches the new artifact image. An artifact category is assigned to the new artifact image based on the matched ideal image. An artifact feature is extracted from the new artifact image according to the assigned category. The image-based diagnostic tool then generates a plurality of metrics for the extracted artifact feature. The metrics are used to identify an artifact image from the plurality of historical images that most closely matches the new artifact image and a corrective action for repairing the unknown fault. A more detailed discussion of the image-based diagnostic tool is set forth in commonly assigned, U.S. patent application Ser. No. 08/921,959 (Attorney Docket No. RD-25,565), filed Aug. 26, 1997, entitled "System And Method For Performing Image-Based Diagnosis", which is incorporated herein by reference.

The waveform data 36 are analyzed with a waveform analysis tool. This tool diagnoses waveform data generated from a machine with a diagnostic knowledge base that stores rules for diagnosing faults and corrective actions for repairing the faults. The waveform analysis tool removes extraneous data from the waveform data and categorizes the waveform data as either normal or faulty. Features are extracted from the waveform data that is categorized as faulty data. The waveform analysis tool isolates a candidate set of faults for the extracted features and identifies root causes most likely responsible for the candidate set of faults from the diagnostic knowledge base. A more detailed discussion of the waveform analysis tool is set forth in commonly assigned, U.S. patent application Ser. No. 09/050,143 (Attorney Docket No. RD-25,897), filed Mar. 30, 1998, entitled "System And Method For Diagnosing And Validating A Machine Using Waveform Data", which is incorporated herein by reference.

The imaging machine's operative parameters 30 are analyzed with a trending tool. The trending tool utilizes the power or temperature data and looks for any abnormal behavior. This is achieved by extracting some basic parameters such as the mean and standard deviation over a variable window size, for the normal "baseline" data. The above analytic and diagnostic tools are an illustrative list of some of the tools that may be used with this invention and not an exhaustive list.

The site specific database 18 contains a plurality of information taken from each imaging machine. Some of the site specific information that is stored in the site specific database 18 are the system ID, the field engineer that worked on the imaging machine, the model type of the machine, the site where the machine is located, the service engineer that helped in diagnosing the machine, and the probe type of the machine. The above site specific information is an illustrative list of some of the fields of information and not an exhaustive list.

Figure 3:
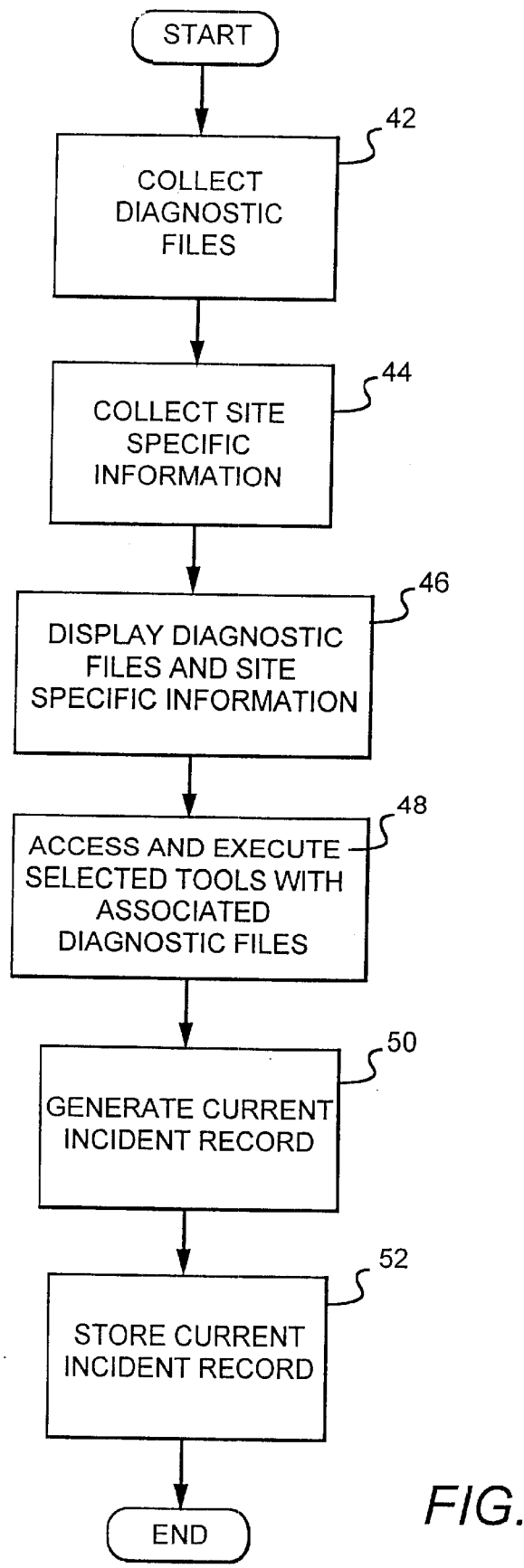
FIG. 3 shows a flow chart setting forth the steps performed by the diagnostic router shown in FIG. 1.

FIG. 3 shows a flow chart setting forth the steps performed by the diagnostic router 12. In particular, the flow chart in FIG. 3 details how the diagnostic router 12 processes the plurality of diagnostic files 14, the site specific information for the machine 16, and the plurality of analytic and diagnostic tools 20. In this invention, the diagnostic router 12 is embedded in a computer such as a workstation. However other types of computers can be used such as a mainframe, a minicomputer, a microcomputer, or a supercomputer. The algorithm performed in the diagnostic router 12 is programmed in C++, JAVA, and MATLAB, but other languages may be used. The diagnostic router begins the processing by collecting the plurality of diagnostics files 14 generated from the machine 16 at 42 and the site specific information for the machine from the site specific database 18 at 44. The diagnostic router 12 displays the diagnostic files 14 and the site specific information to a user such as a service engineer at 46. The service engineer selects a number of the analytic and diagnostic tools 20 to evaluate the diagnostic files 14 and the site specific information. The diagnostic router accesses and executes each of the analytic and diagnostic tools selected by the service engineer at 48. Each of the analytic and diagnostic tools generates an output which contains a list of recommendation(s) for diagnosing the condition for the malfunction. The diagnostic router 12 generates a current incident record from the diagnostic files 14, the site specific information, and the tool outputs at 50. The current incident record is then stored in the current incident record database 22 at 52.

An example of a current incident record 54 is shown in FIG. 4. This current incident record contains site specific information 56 which indicates the system ID, the site where the machine is located, the model type of the machine, the modality, the field engineer that worked on the imaging machine, the date, and the probe type of the machine. The current incident record 54 also contains the diagnostic files generated from the machine 16, the analytic and diagnostic tools 20 used to evaluate the information, and the tool outputs. The diagnostic files, the tools, and the tool outputs are represented in FIG. 4 collectively as reference numeral 58. In this example, the diagnostic files that were obtained were image files and error logs and these files were evaluated by an image-based diagnostic tool and an error log similarity index tool, respectively.

Figure 5:
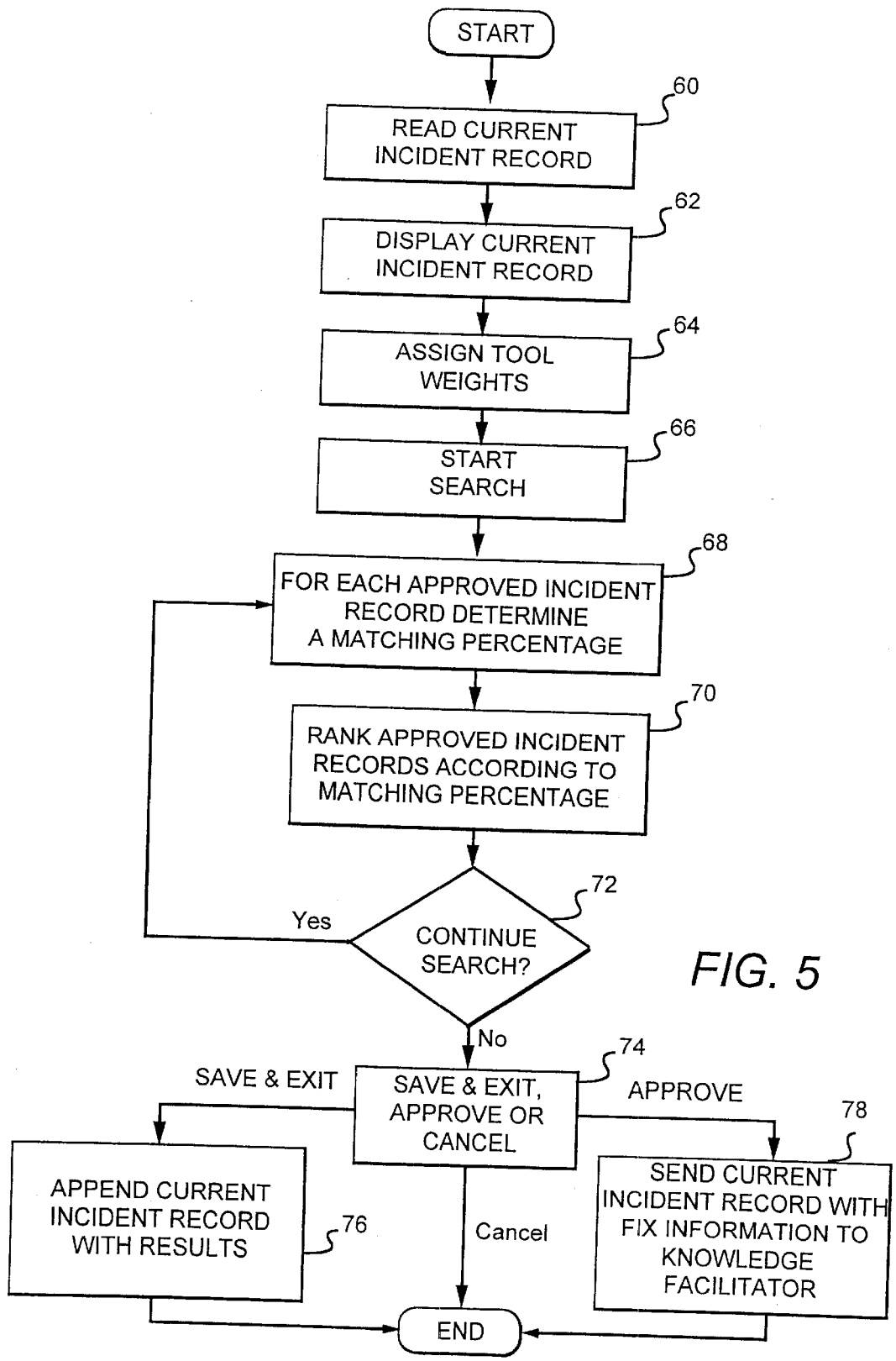
FIG. 5 shows a flow chart setting forth the steps performed by the integrator shown in FIG. 1.

FIG. 5 shows a flow chart setting forth the steps performed by the integrator 24. In particular, the flow chart in FIG. 5 details how the integrator 24 processes the current incident record 54 and finds approved incident records from the approved incident record database 26 that most closely match the current incident record. In this invention, the integrator is embedded in a computer such as a workstation. However other types of computers can be used such as a mainframe, a minicomputer, a microcomputer, or a supercomputer. The algorithm performed in the integrator is programmed in C++, JAVA, and MATLAB, but other languages may be used. The integrator 24 begins the processing by reading the current incident record 54 from the current incident record database 22 at 60. The integrator 24 displays the current incident record 54 to the service engineer at 62. The service engineer assigns a tool weight for each of the diagnostic and analytic tools 20 at 64. The weight is representative of the confidence that the service engineer has in the tool to solve the current incident record.

The integrator 24 starts the search for approved incident records in the approved incident record database 26 that most closely match the current incident record at 66. Each of the approved incident records in the approved incident record database 26 contains historical tool outputs generated from the diagnostic and analytic tools 20. For each approved incident record in the incident record database 26, the integrator 24 determines a matching percentage with the current incident record according to the weights assigned to each of the tools at 68. The integrator 24 ranks the approved incident records according to the determined matching percentage at 70. The integrator 24 ranks all of the approved incident records in the approved incident record database 26 according to the matching percentage unless instructed by the service engineer to stop the search at 72.

After the search has been stopped, there are three options for the service engineer at 74. The options are to save the current incident record, to approve the highest ranked approved incident record, or to cancel. If it is desired to save the current incident record, then the current incident record is appended with the results from the highest ranked approved incident record at 76 and stored in the current incident record database. To approve the results from the highest ranked incident record, the necessary fix information is added to the current incident record and sent to a knowledge facilitator at 78. The knowledge facilitator then decides whether the current incident record should be stored in the approved incident record database 26 and used in future cases.

An example of a graphical user-interface 80 for the integrator 24 is shown in FIG. 6. The graphical user-interface 80 displays the site specific information for the imaging machine 16. The various tool recommendations for each selected analytic and diagnostic tool 20 along with a confidence value indicating the confidence that the recommended action will correct the failure, the fault condition, or the symptoms of the incipient failure, are also displayed. In order to integrate this information, the tool diagnostic outputs are in the form of one or preferably, two tuples. In particular, the tool recommendation that classifies the symptoms (i.e., a particular field replaceable unit, FRU) as a particular failure condition is one tuple, while the confidence value assigned to the particular recommendation is two tuple. This information is then used for matching with the approved incident records in the approved incident record database. An example is shown in Table 1. In this example, ELSI and IDIA are the analytic and diagnostic tools.

TABLE 1

| ELSI  | Confidence Level | IDIA       | Rank |
|-------|------------------|------------|------|
| FRU A | 0.8              | Artifact A | 1    |
| FRU B | 0.5              | Artifact B | 2    |
| FRU C | 0.1              |            |      |

The graphical user-interface 80 also includes a section for assigning a tool weight for each of the diagnostic and analytic tools. As mentioned above, the weight is representative of the confidence that the service engineer has in the tool to solve the current incident record. Generally, there are three options for selecting a weight. The first option is to assign a default weight which is based on the prior history of the respective tools. For this option, the tools are initially assigned an equal weight such as 1.0, however, as the integrator is used more often the weights change. The second option is for the service engineer to define the weights. In this case, the service engineer defines weights ($w_{t_k}$, wherein k is the number of tools in current incident record, and $t_k$ is the tool $t_1$, $t_2$, $t_3$, etc.) for the tools based on his/her experience. This is done to ensure that a service engineer's prior knowledge about cases similar to the one being handled currently is utilized and is incorporated in the analysis of the current incident record. For example, if the service engineer decides that under certain conditions, a particular tool has better diagnostic capabilities, then the outputs of that tool are weighed more heavily. The third option is to assign equal weights or no weights. This is done when either the integrator or the service engineer cannot differentiate between the capabilities of the tools for the current incident record.

After the weights have been assigned, the search for approved incident records in the approved incident record database 26 that most closely match the current incident record is initiated. In this invention, a case-based reasoning algorithm is used to find cases (i.e., approved incident records) having similar attributes to the current situation (i.e., current incident record). Preferably, this is done by using a search procedure that uses search strings of three tuple. For example, the search strings of three tuple are either the (tool, FRU, rank), or the (tool, artifact, rank) or (tool, subsystem, rank) from the current incident record. The rank in these three tuples is the rank that is given to the FRU, artifact or subsystem by the particular tool. The individual tool outputs are ranked in decreasing order of confidence by all of the individual tools. As described in the following sections, it is preferable that the tool outputs are at the FRU level, and each tool output is assigned a confidence level by the tool.

In this invention, the search strings are not limited to three tuple, and other enhancements are possible, depending on the individual tool properties. For example, for the error log similarity index tool, a confidence level character is used to confirm the match between the error log similarity index tool output in the approved incident record and the current incident record. For the trending tool, the three tuple comprises (tool, string, duration).

The approved incident record database 26 is searched using the three tuple of the current incident record to find the best match. In this invention, matching percentages are assigned to all tool outputs of each individual tool. The matching percentages are based on the number of fields matched in that particular approved incident record. This matching percentage is then used to rank the approved incident records in decreasing order of matching percentage. A default list of the ten closest matching approved incident records is provided. However, the service engineer has the flexibility to define the number of closest matching approved incident records as desired.

There are many techniques that have been implemented for matching strings, numbers, etc. However, any search methodology is limited by its database. For instance, considering the aspects of this invention, if the database is not comprehensive enough to cover all possible scenarios, or the tool outputs of the individual tools are not identical in the approved incident record and the current record for the same type of faults, then the resulting recommendation will be limited in its accuracy.

These problems are prevalent in classical relational databases. A classical relational database comprises a series of n-dimensional relations which are conceptualized as tables. The columns of these tables correspond to fields or attributes, and are referred to as domains. Each domain is defined on an appropriate domain base or universal set. The rows are elements of the relation and correspond to records, which are called tuples. A classical relational database is limited by the fact that it cannot handle parsed datasets or incomplete information. The classical relational database model provides a crisp equivalence relation, defined on each domain universal set which groups together elements which are strictly equivalent. In a classical database, equivalence classes generated by this relation are simply the singletons of the universal set. Thus, a result of a match between a current incident record and an approved incident record is either TRUE or FALSE. This approach does not allow one to define a "close" match between the current incident record and the approved incident record.

In order to overcome this problem, this invention uses a fuzzy relational database for the approved incident record database 26. The advantage of the fuzzy relational database over the classical relational database is that it allows relations which are not just singletons but are generalized to fuzzy similarity relations. This provides flexibility and allows for partial matching between the rows and the columns. This is helpful in matching incident records which are not identical to the ones existing in the approved incident record database 26. Table 2 shows a simple example of a classical and a fuzzy relational database.

TABLE 2

Classical and Fuzzy Relational Database

| AGE | Young (Classical) | Young (Fuzzy) |
|-----|-------------------|---------------|
| 10  | 1.0               | 1.0           |
| 20  | 1.0               | 0.7           |
| 30  | 0.0               | 0.4           |
| 40  | 0.0               | 0.0           |

For each approved incident record in the incident record database 26, the integrator 24 determines a matching percentage with the current incident record according to the weights assigned to each of the tools. The matching percentages are determined for all tool outputs from an individual tool. The matching percentages are based on the number of fields matched in that particular approved incident record. In this invention, a fuzzy relational matrix is used to match the rank of the tool outputs in the current incident record with the rank of the tool output in the approved incident records. The equation for the fuzzy relational matrix for a tool output match is:

$$t_i = \min(w_{n,n} - w_{m,m}) - [abs(m-n)*abs(w_{m,m} - w_{n,n})/\max(m,n)]*100$$

wherein n is the rank of the tool output in the current incident record, m is the rank of the tool output in the approved incident record, w is the fuzzy relational matrix, $w_{n,n}$ is the element at the $n^{th}$ row and the $n^{th}$ column, $t_i$ is the single tool output matching percentage, and i is the individual rank within each tool. Note that there is no term for $w_{m,n}$ in the above equation because it is tailored for tools which do not provide any confidence value associated with their recommendations. In that case, no distinction is made between the first and the second ranked output. Hence, when comparing two incident records, the only correct solution is when a match is found, and there is no "belief" associated with no match between the different incident records. The fuzzy relational matrix enables one to rank the individual tool outputs of the current incident record.

The fuzzy relational matrix is determined by using the diagonal for the weighing matrix (i.e., the matrix for which the w's are calculated). For example, assume that the elements of the diagonal are as follows:

$$w_{1,1}=1; \; w_{2,2}=0.75; \; w_{3,3}=0.6; \; w_{4,4}=0.5; \; w_{5,5}=0.45$$

This implies that if a tool output from the current incident record is compared to a tool output from an approved incident record, and if both the tool outputs of that particular tool are ranked first, then there is a 100% match. On the other hand, if both tool outputs are ranked fifth, then the matching percentage is only 45%. This is done to differentiate between a one-to-one match (i.e., a perfect match) and a fifth-to-fifth match. Accordingly, the complete fuzzy relational matrix for this case is defined as:

$$W_{m,n} = \begin{vmatrix} 1 & 0.625 & 0.33 & 0.125 & 0.01 \\ 0.625 & 0.75 & 0.55 & 0.375 & 0.27 \\ 0.33 & 0.55 & 0.6 & 0.475 & 0.39 \\ 0.125 & 0.375 & 0.475 & 0.5 & 0.44 \\ 0.01 & 0.27 & 0.39 & 0.44 & 0.45 \end{vmatrix}$$

This fuzzy relational matrix only has five columns and five rows, implying that any individual tool output rank greater than five does not provide any meaningful information and is not considered in the analysis. This fuzzy relational matrix can also be written as follows:

$$W_{m,n} = 0, \forall m > 5, n > 5$$

This fuzzy relational matrix provides the maximum matching value when there is a perfect match between the tool prediction of the current incident record and the tool prediction of the approved incident record.

The individual tool output percentages ($t_i$) are combined to obtain the tool matching percentage ($T_i$), which is defined as:

$$T_i = \frac{(t_1 + t_2 + \ldots + t_k)}{N_f}$$

wherein $t_k$ is the $k^{th}$ tool output of $1^{th}$ tool of the current incident record and $N_f$ is the normalizing factor for a tool which is defined as:

$$N_{f=w1,1} + w_{2,2} + \ldots + w_{k,k}$$

An example of the above fuzzy relational matrix ($W_{m,n}$) applied to a current incident record with a tool output of [$FRU_1$, $FRU_4$, $Artifact_A$, $FRU_8$, $FRU_2$] is now presented. Assuming that a particular approved incident record has a tool output of [$FRU_1$, $FRU_4$, $Artifact_A$, $FRU_8$, $FRU_2$], which is identical to the tool output of the current incident record, the matching percentage for this particular case is:

$$w_{1,1}=1; \; w_{2,2}=0.75; \; w_{3,3}=0.6; \; w_{4,4}=0.5; \; w_{5,5}=0.45.$$

This results in a total matching percentage of 330%. Thus, a normalizing factor ($N_f$=3.3) is used to scale all matching percentages to 100% for each tool. The different tool matching percentages are averaged to calculate the matching percentage between the current incident record and the approved incident record. The matching percentage for the current incident record with that particular approved incident record is calculated as follows:

$$M_l = \frac{\sum_{n=1}^{k} T_n}{k}$$

wherein k is the number of tools in the current incident record, $M_l$ is matching percentage of the current incident record with the $l^{th}$ approved incident record, and $T_n$ is the tool matching percentage for each tool. This process is repeated with the other approved incident records to rank the closest matching incident records.

This invention is not limited to the above described fuzzy relational matrix, and other modifications are possible in view of the difference in tool outputs for each of the analytic and diagnostic tools 20. For example, the error log similarity index tool provides a confidence level in the match, which adds another dimension to the fuzzy relational matrix. When an error log similarity index tool output in the current incident record with a confidence factor ($C_1$) is compared with an error log similarity index tool output in the approved incident record with a confidence factor ($C_2$), then several steps are taken. First, the confidence factor of the current incident record ($C_1$) and the approved record ($C_2$) is compared. In this case, the higher confidence factor of ($C_1$, $C_2$) is used in the fuzzy membership function to determine which fuzzy relational matrix ($W_1$, $W_2$, $W_3$) should be used and to what degree. The matching percentage is calculated as follows:

$$t_i = (d_{high}*W1_{(m,n)} + d_{medium}*W2_{(m,n)} + d^{low}*W3_{(m,n)})*(1-abs(C1-C2))*100,$$

wherein $t_i$ is the matching percentage between the first output of the error log similarity index tool in the current incident record and the first output of the error log similarity index tool in an approved incident record; $W_1$, $W_2$, $W_3$ are the relational matrices for High, Medium, Low membership functions; $W_1=0.8*W_2$ and $W_3=0.6*W_1$; n is the rank of the tool output in the current incident record; m is the rank of the tool output in the approved incident record; $d_{high}$, $d_{medium}$, $d_{low}$ are the degree to which each membership function is fired; and C1, C2 are the confidence values for an error log similarity index tool output for current and approved incident records.

Figure 7:
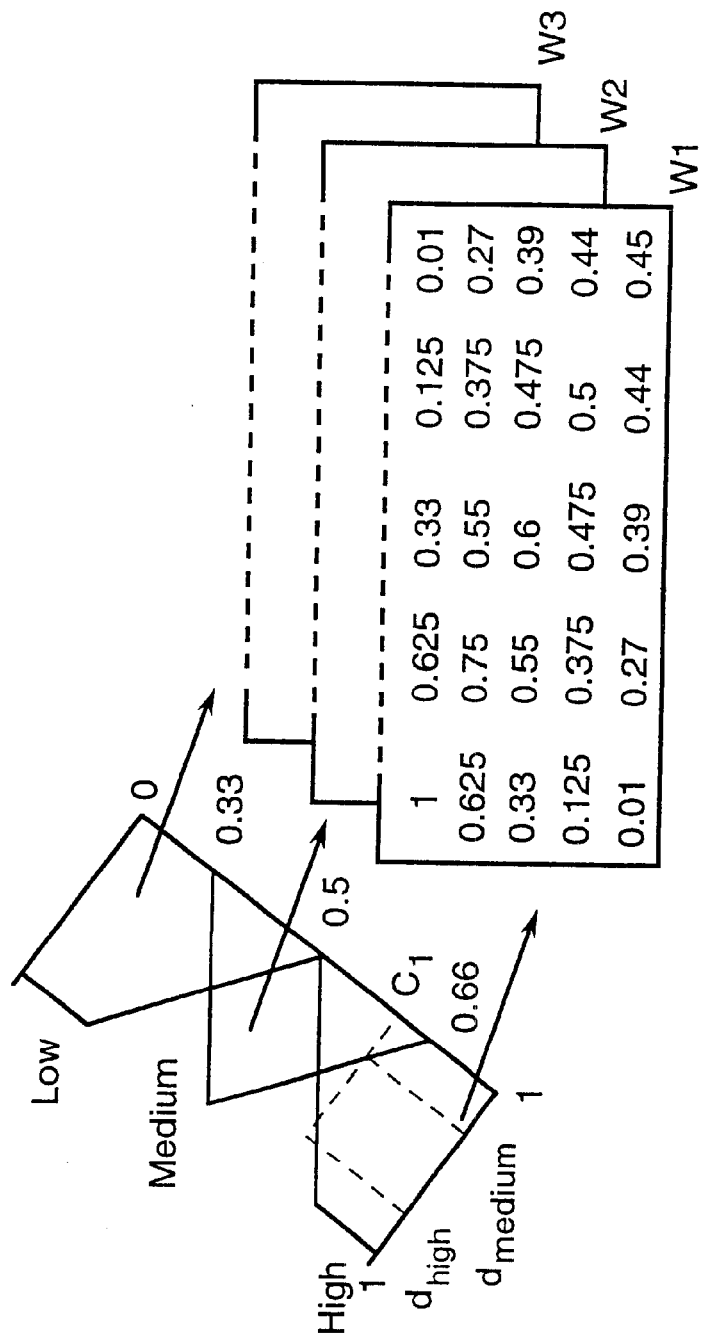
FIG. 7 shows an example of combining a fuzzy membership function for a confidence factor with a ranking matrix according to this invention.

An example showing how the confidence factor and the ranking matrix are combined is shown in FIG. 7. Once the weighing matrices are calculated as described above, then the ranking of the current incident record tool output is matched with the corresponding ranking of the approved incident record tool output. Then a multiplying factor is calculated using fuzzy membership functions. This is determined by using the confidence associated with the tool output.

Once a percentage is assigned to each approved incident record in the approved incident record database 26, then the integrator 24 lists the approved incident records in decreasing order of their matching percentage with the current incident record. The actual fixes of these approved incident records are the best possible solutions for the current incident record. All of the tool outputs which are not listed in the list of approved incident record actual fixes are appended at the end of this list.

Below is an example illustrating how the integrator 24 assimilates a current incident record and finds approved incident records from the approved incident record database that most closely match the current incident record. The current incident record is shown below in Table 3.

TABLE 3

| ELSI | Confidence Level | IDIA | Rank |
|---|---|---|---|
| FRU A | 0.8 | Artifact A | 1 |
| FRU B | 0.5 | Artifact B | 2 |
| FRU C | 0.1 | | |

The approved incident database is shown in Tables 4 and 5.

TABLE 4

| | APPROVED IR 1 | | APPROVED IR 2 | |
|---|---|---|---|---|
| TOOL | Tool Output | Confidence Level/Rank | Tool Output | Confidence Level/Rank |
| ELSI | FRU D | 0.9 | FRU A | 0.8 |
| | FRU X | 0.8 | FRU C | 0.5 |
| | FRU B | 0.7 | | |
| IDIA | Artifact B | 1 | Artifact E | 1 |
| | Artifact D | 2 | Artifact A | 2 |
| | Artifact A | 3 | Artifact X | 3 |

TABLE 5

| | APPROVED IR 3 | | APPROVED IR 4 | |
|---|---|---|---|---|
| TOOL | Tool Output | Confidence Level/Rank | Tool Output | Confidence Level/Rank |
| ELSI | FRU A | 0.7 | FRU D | 0.9 |
| | FRU B | 0.5 | FRU E | 0.9 |
| IDIA | Artifact A | 1 | Artifact X | 1 |
| | Artifact D | 2 | Artifact Y | 2 |

Next, the matching percentage for each approved incident record with the current record is calculated. For example, the matching percentage for the approved incident record IR3 and the current incident record is determined in the following manner. The values for the error log similarity index tool (ELSI), (1, FRU A-0.8, 1, FRU A-0.7) are substituted in the following equation:

$$t_i = (d_{high}*W1_{(m,n)} + d_{medium}*W2_{(m,n)} + d_{low}*W3_{(m,n)})*(1-abs(C1-C2))*100$$

such that $$t_1 = (1.0*1.0 + 0.0*0.0 + 0.0*0.0)*(1-abs(0.8-0.7))*100 = 90\%$$

For ELSI, (1, FRU B-0.5, 1, FRU B-0.6):

$$t_2 = (1.0*0.0 + 1.0*0.8 + 0.0*0.0)*(1-abs(0.5-0.5))*100 = 80\%$$

Hence, the matching percentage for ELSI is (90+80)/2 = 85%. Similarly, the matching percentage for the image-based diagnosis tool IDIA results in 100%, and the matching percentage for the approved incident record IR3 with the current incident record is 92.5%. The matching percentage for all of the approved incident records IR1–IR4 with the current incident record is provided in Table 6.

TABLE 6

Matching Percentage With Current Incident Record

| | ELSI | IDIA | Average |
|---|---|---|---|
| Approved IR1 | 18.723 | 61.71 | 40.217 |
| Approved IR2 | 50.937 | 35.71 | 43.33 |
| Approved IR3 | 85 | 100 | 92.5 |
| Approved IR4 | 0 | 0 | 0 |

The actual fixes for the best approved incident records (i.e., IR3, IR2, IR1) are then obtained and provided by the integrator as a final listing of recommendations to diagnose the imaging machine. The actual fixes are set forth in Table 7.

TABLE 7

Actual Fix Of Approved IR3
Actual Fix Of Approved IR2
Actual Fix Of Approved IR1

It is therefore apparent that there has been provided in accordance with the present invention, a system and method for integrating a plurality of diagnostic related information that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

What is claimed is:

1. A system for integrating a plurality of information from a multiple of sources, comprising:

a site specific database containing site specific information for a machine;

a plurality of diagnostic related information obtained from the machine;

a plurality of diagnostic and analytic tools for evaluating the plurality of diagnostic related information, wherein each diagnostic and analytic tool generates a tool output containing a list of possible recommendations pertaining to the machine;

a diagnostic router for collecting site specific information for the machine from the site specific database and the plurality of diagnostic related information and generating a current incident record therefrom;

an approved incident record database containing a plurality of approved incident records obtained from a plurality of machines; and an integrator for finding approved incident records from the approved incident record database that most closely match the current incident record.

2. The system according to claim 1, wherein the diagnostic router comprises means for accessing the plurality of diagnostic and analytic tools.

3. The system according to claim 2, wherein the diagnostic router comprises means for executing the diagnostic and analytic tools according to a user specified selection.

4. The system according to claim 3, wherein the diagnostic router comprises means for collecting the tool outputs generated from each of the diagnostic and analytic tools and putting the tool outputs into the current incident record.

5. The system according to claim 4, wherein the diagnostic router comprises means for storing the current incident record in a current incident record database.

6. The system according to claim 1, wherein the integrator comprises means for displaying the current incident record.

7. The system according to claim 2, wherein the integrator comprises means for assigning a weight to each of the plurality of diagnostic and analytic tools, the weight being representative of the confidence in the tool to solve the current incident record.

8. The system according to claim 7, wherein the integrator comprises means for searching through the approved incident record database for approved incident records that most closely match the current incident record.

9. The system according to claim 8, wherein each of the plurality of approved incident records in the approved incident record database contains historical tool outputs generated from diagnostic and analytic tools used to evaluate the plurality of machines.

10. The system according to claim 9, wherein the integrator comprises means for determining a matching percentage between the current incident record and each of the approved incident records in the approved incident record database according to the weights assigned for each of the diagnostic and analytic tools.

11. The system according to claim 10, wherein the integrator comprises means for ranking the approved incident records according to the matching percentage.

12. The system according to claim 11, wherein the integrator comprises means for stopping the search according to a user selection.

13. The system according to claim 12, wherein the integrator comprises means for appending the current incident record with data from the approved incident record that most closely matches the current incident record.

14. The system according to claim 13, wherein the integrator comprises means for storing the appended current incident record in the approved incident record database.

15. The system according to claim 12, wherein the integrator comprises means for storing the current incident record in a current incident record database.

16. The system according to claim 1, wherein the machine and the plurality of machines are medical imaging machines.

17. A method for integrating a plurality of information from a multiple of sources, comprising the steps of:

storing site specific information for a machine;

receiving a plurality of diagnostic related information obtained from the machine;

accessing a plurality of diagnostic and analytic tools for evaluating the plurality of diagnostic related information, wherein each diagnostic and analytic tool generates a tool output containing a list of possible recommendations pertaining to the machine;

collecting site specific information for the machine and the plurality of diagnostic related information and generating a current incident record therefrom;

storing a plurality of approved incident records obtained from a plurality of machines; and finding approved incident records that most closely match the current incident record.

18. The method according to claim 17, wherein the step of collecting further comprises executing the diagnostic and analytic tools according to a user specified selection.

19. The method according to claim 18, further comprising collecting the tool outputs generated from each of the diagnostic and analytic tools and putting the tool outputs into the current incident record.

20. The method according to claim 19, further comprising storing the current incident record in a current incident record database.

21. The method according to claim 17, wherein the step of finding comprises displaying the current incident record.

22. The method according to claim 17, wherein the step of finding comprises assigning a weight to each of plurality of diagnostic and analytic tools, the weight being representative of the confidence in the tool to solve the current incident record.

23. The method according to claim 22, wherein the step of finding comprises searching for approved incident records that most closely match the current incident record.

24. The method according to claim 23, wherein each of the plurality of approved incident records contains historical tool outputs generated from diagnostic and analytic tools used to evaluate the plurality of machines.

25. The method according to claim 24, wherein the step of finding comprises determining a matching percentage between the current incident record and each of the approved incident records according to the weights assigned for each of the diagnostic and analytic tools.

26. The method according to claim 25, wherein the step of finding further comprises ranking the approved incident records according to the matching percentage.

27. The method according to claim 26, wherein the step of finding further comprises stopping the search according to a user selection.

28. The method according to claim 27, wherein the step of finding further comprises appending the current incident record with data from the approved incident record that most closely matches the current incident record.

29. The method according to claim 28, wherein the step of finding further comprises storing the appended current incident record with the plurality of approved incident records.

30. The method according to claim 27, wherein the step of finding further comprises storing the current incident record in a current incident record database.

31. The method according to claim 17, wherein the machine and plurality of machines are medical imaging machines.

32. A system for integrating a plurality of information from a multiple of sources to facilitate monitoring and diagnosis of a medical imaging machine, comprising:

a site specific database containing site specific information for the medical imaging machine;

a plurality of diagnostic related information obtained from the medical imaging machine;

a plurality of diagnostic and analytic tools for evaluating the plurality of diagnostic related information, wherein each diagnostic and analytic tool generates a tool output containing a list of possible recommendations pertaining to the medical imaging machine;

a diagnostic router for collecting site specific information for the medical imaging machine from the site specific database and the plurality of diagnostic related information and generating a current incident record therefrom;

an approved incident record database containing a plurality of approved incident records obtained from a plurality of medical imaging machines; and an integrator for finding approved incident records from the approved incident record database that most closely match the current incident record.

33. The system according to claim 32, wherein the diagnostic router comprises means for accessing the plurality of diagnostic and analytic tools.

34. The system according to claim 33, wherein the diagnostic router comprises means for executing the diagnostic and analytic tools according to a user specified selection.

35. The system according to claim 34, wherein the diagnostic router comprises means for collecting the tool outputs generated from each of the diagnostic and analytic tools and putting the tool outputs into the current incident record.

36. The system according to claim 35, wherein the diagnostic router comprises means for storing the current incident record in a current incident record database.

37. The system according to claim 32, wherein the integrator comprises means for displaying the current incident record.

38. The system according to claim 33, wherein the integrator comprises means for assigning a weight to each of the plurality of diagnostic and analytic tools, the weight being representative of the confidence in the tool to solve the current incident record.

39. The system according to claim 38, wherein the integrator comprises means for searching through the approved incident record database for approved incident records that most closely match the current incident record.

40. The system according to claim 39, wherein each of the plurality of approved incident records in the approved incident record database contains historical tool outputs generated from diagnostic and analytic tools used to evaluate the plurality of medical imaging machines.

41. The system according to claim 40, wherein the integrator comprises means for determining a matching percentage between the current incident record and each of the approved incident records in the approved incident record database according to the weights assigned for each of the diagnostic and analytic tools.

42. The system according to claim 41, wherein the integrator comprises means for ranking the approved incident records according to the matching percentage.

43. The system according to claim 42, wherein the integrator comprises means for stopping the search according to a user selection.

44. The system according to claim 43, wherein the integrator comprises means for appending the current incident record with data from the approved incident record that most closely matches the current incident record.

45. The system according to claim 44, wherein the integrator comprises means for storing the appended current incident record in the approved incident record database.

46. The system according to claim 43, wherein the integrator comprises means for storing the current incident record in a current incident record database.

47. A method for integrating a plurality of information from a multiple of sources to facilitate monitoring and diagnosis of a medical imaging machine, comprising the steps of:

storing site specific information for the medical imaging machine;

receiving a plurality of diagnostic related information obtained from the medical imaging machine;

accessing a plurality of diagnostic and analytic tools for evaluating the plurality of diagnostic related information, wherein each diagnostic and analytic tool generates a tool output containing a list of possible recommendations pertaining to the medical imaging machine;

collecting site specific information for the medical imaging machine and the plurality of diagnostic related information and generating a current incident record therefrom;

storing a plurality of approved incident records obtained from a plurality of medical imaging machines; and finding approved incident records that most closely match the current incident record.

48. The method according to claim 47, wherein the step of collecting further comprises executing the diagnostic and analytic tools according to a user specified selection.

49. The method according to claim 48, further comprising collecting the tool outputs generated from each of the diagnostic and analytic tools and putting the tool outputs into the current incident record.

50. The method according to claim 49, further comprising storing the current incident record in a current incident record database.

51. The method according to claim 47, wherein the step of finding comprises displaying the current incident record.

52. The method according to claim 47, wherein the step of finding comprises assigning a weight to each of plurality of diagnostic and analytic tools, the weight being representative of the confidence in the tool to solve the current incident record.

53. The method according to claim 52, wherein the step of finding comprises searching for approved incident records that most closely match the current incident record.

54. The method according to claim 53, wherein each of the plurality of approved incident records contains historical tool outputs generated from diagnostic and analytic tools used to evaluate the plurality of medical imaging machines.

55. The method according to claim 54, wherein the step of finding comprises determining a matching percentage between the current incident record and each of the approved incident records according to the weights assigned for each of the diagnostic and analytic tools.

56. The method according to claim 55, wherein the step of finding further comprises ranking the approved incident records according to the matching percentage.

57. The method according to claim 56, wherein the step of finding further comprises stopping the search according to a user selection.

58. The method according to claim 57, wherein the step of finding further comprises appending the current incident record with data from the approved incident record that most closely matches the current incident record.

59. The method according to claim 58, wherein the step of finding further comprises storing the appended current incident record with the plurality of approved incident records.

60. The method according to claim 57, wherein the step of finding further comprises storing the current incident record in a current incident record database.

* * * * *